US012799455B2

(12) United States Patent
Offner et al.

(10) Patent No.: US 12,799,455 B2
(45) Date of Patent: Nov. 17, 2026

(54) METHOD FOR THE PRODUCTION OF THYMOCYTE SUPERNATANT

(71) Applicant: Hoffmann-La Roche Inc., Little Falls, NJ (US)

(72) Inventors: Sonja Offner, Penzberg (DE); Markus Horvath, Penzberg (DE); Ingried Saam, Marnbach (DE)

(73) Assignee: Hoffmann-La Roche Inc., Branchburg, NJ (US)

(*) Notice: Subject to any disclaimer, the term of this patent is extended or adjusted under 35 U.S.C. 154(b) by 25 days.

(21) Appl. No.: 18/389,801

(22) Filed: Dec. 20, 2023

(65) Prior Publication Data

US 2024/0117308 A1 Apr. 11, 2024

Related U.S. Application Data

(60) Division of application No. 16/591,351, filed on Oct. 2, 2019, now Pat. No. 11,891,624, which is a continuation of application No. PCT/EP2018/062647, filed on May 16, 2018.

(30) Foreign Application Priority Data

May 19, 2017 (EP) .................................... 17171903

(51) Int. Cl.
*C12N 5/0781* (2010.01)

(52) U.S. Cl.
CPC ........ *C12N 5/0635* (2013.01); *C12N 2500/30* (2013.01); *C12N 2501/998* (2013.01); *C12N 2501/999* (2013.01); *C12N 2502/1114* (2013.01); *C12N 2502/1157* (2013.01); *C12N 2502/1185* (2013.01)

(58) Field of Classification Search
None
See application file for complete search history.

(56) References Cited

U.S. PATENT DOCUMENTS

| | | | |
|---|---|---|---|
| 5,010,182 | A | 4/1991 | Brake et al. |
| 5,637,677 | A | 6/1997 | Greene et al. |
| 7,807,415 | B2 | 10/2010 | Groen et al. |

(Continued)

FOREIGN PATENT DOCUMENTS

| | | | |
|---|---|---|---|
| AU | 2002223505 | B2 | 5/2002 |
| AU | 2012203085 | A1 | 6/2012 |

(Continued)

OTHER PUBLICATIONS

Seeber, Stefan; et al; "A Robust High Throughput Platform to Generate Functional Recombinant Monoclonal Antibodies Using Rabbit B Cells from Peripheral Blood" PLoS One, 9, e86184, 2014 (Year: 2014).*

(Continued)

*Primary Examiner* — David W Berke-Schlessel
(74) *Attorney, Agent, or Firm* — Robert K. Rodriguez

(57) ABSTRACT

Herein is reported a method for producing a thymocyte supernatant comprising the steps of co-cultivating thymocytes and mononuclear cells at a cell ratio of at least 0.5:1.2 in the presence of phorbol-12-myristate-13-acetate and Phytohemagglutinin M for up to 60 hours, and separating the co-cultivation medium from the cells and thereby producing the thymocyte supernatant.

8 Claims, 1 Drawing Sheet

(56) References Cited

U.S. PATENT DOCUMENTS

| | | | |
|---|---|---|---|
| 2006/0051348 | A1 | 3/2006 | Gorlach |
| 2006/0258842 | A1 | 11/2006 | Groen et al. |
| 2007/0098711 | A1 | 5/2007 | Groen et al. |
| 2007/0269868 | A1 | 11/2007 | Jensen et al. |
| 2013/0084637 | A1 | 4/2013 | Endl et al. |
| 2013/0177987 | A1 | 7/2013 | Schram et al. |
| 2019/0144942 | A1 | 5/2019 | Shalek et al. |
| 2020/0165566 | A1 | 5/2020 | Offner et al. |

FOREIGN PATENT DOCUMENTS

| | | | |
|---|---|---|---|
| CA | 2587817 | A1 | 5/2006 |
| EP | 0362179 | A2 | 4/1990 |
| EP | 0362179 | A3 | 4/1990 |
| EP | 0488470 | A1 | 6/1992 |
| WO | 1999/42077 | A2 | 8/1999 |
| WO | 2007/031550 | A2 | 3/2007 |
| WO | 2008/045140 | A1 | 4/2008 |
| WO | 2008/144763 | A2 | 11/2008 |
| WO | 2011/147903 | A1 | 12/2011 |
| WO | 2012/178150 | A2 | 12/2012 |
| WO | 2012/178150 | A3 | 12/2012 |
| WO | 2013/076139 | A1 | 5/2013 |
| WO | 2015/000624 | A1 | 1/2015 |
| WO | 2017/167714 | A1 | 10/2017 |
| WO | 2019/079361 | | 4/2019 |

OTHER PUBLICATIONS

Clackson, T., et al., "Making antibody fragments using phage display libraries" Nature 352(6336):624-628 (Aug. 15, 1991).
"International Preliminary Report on Patentability—PCT/EP2018/062647":pp. 1-10 (Nov. 28, 2019).
"International Search Report—PCT/EP2018/062647":pp. 1-16 (Jun. 28, 2018).
Kindt et al. Antigens and Antibodies "4" (14 pages), 6th edition, N.Y.:W.H. Freeman and Co, :p. 91 (2007).
Kwekkeboom, J. et al., "An efficient procedure for the generation of human monoclonal antibodies based on activation of human B lymphocytes by a murine thymoma cell line" J Immunol Meth 160(1):117-127 (Jan. 1, 1993).
Long, J., "Studies on Proliferation on promoting Effect of Supernatant from Human Thymic Epithelial Cell Culture on Mouse Thymocyte and T-Cell Line" Develop & Reprod Biology—China 6(2):53-58 (Dec. 1, 1997).
Masri, S., et al., "Cloning and expression in *E. coli* of a functional Fab fragment obtained from single human lymphocyte against anthrax toxin" Molec Immunol 44(8):2101-2106 (Mar. 1, 2007).
Miyahira, A.,, "Types of Immune cells present in Human PBMC" Sanguine Bioscience Blog (Web page accessed May 7, 2017),:1-4 (Nov. 22, 2012).
Morgan, D., et al., "Antibody-Induced Down-Regulation of a Mutated Insulin Receptor Lacking an Intact Cytoplasmic Domain" Biochemistry 26(11):2959-2963 (Jun. 2, 1987).
Pak, S., et al., "Super-CHO—A cell line capable of autocrine growth under fully defined protein-free conditions" Cytotechnology 22(1-3):139-146 (Jan. 1, 1996).
Paus, D., et al., "Antigen recognition strength regulates the choice between extrafollicular plasma cell and germinal center B cell differentiation" J Exp Med 203(4):1081-1091 (Apr. 17, 2006).
Portolano, S., et al., "Lack of promiscuity in autoantigen-specific H and L chain combinations as revealed by human H and L chain 'Roulette"' J Immunol 150(3):880-887 (Feb. 1, 1993).
Sambrook et al. Molecular Cloning 2nd edition, Cold Spring Harbor Laboratory Press, ( 1989).
Schroeder, Jr., H. et al., "Structure and evolution of mammalian VH families" Int Immunol 2(1):41-50 (Sep. 19, 1989).
Seeber, S., et al., "A robust high throughput platform to generate functional recombinant monoclonal antibodies using rabbit B cells from peripheral blood" PLoS One 9(2):e86184 (1-14) (Feb. 4, 2014).
Seet, C., et al., "Generation of mature T cells from human hematopoietic stem and progenitor cells in artificial thymic organoids" Nat Methods 14(5):521-530 (Apr. 3, 2017).
Smith, K., et al., "The extent of affinity maturation differs between the memory and antibody-forming cell compartments in the primary immune response" EMBO J 16(11):2996-3006 (Jun. 2, 1997).
Steenbakkers, P., et al., "Efficient generation of monoclonal antibodies from preselected antigen-specific B cells" Mol Biol Rep 19(2):125-134 (Mar. 1, 1994).
Tang, "Molecular mechanism of TRPC1 regulating the development of cardiac hypertrophy using human pluripotent stem cell-derived cardiomyocyte model" (Dissertation), pp. 1-96 (Date of oral defence Aug. 21, 2018).
Verma, D., et al., "Monocyte-Macrophage Modulation of T-lymphocyte-Derived Colony-Stimulating Activity Elaboration in Man" Scand J Haematol 28(3):254-263 (Mar. 1, 1982).
Weber, M., et al., "Combining EL4-B5-based B-cell stimulation and phage display technology for the successful isolation of human anti-Scl-70 autoantibody fragments" J Immunol Meth 278(1-2):249-259 (Jul. 1, 2003).
Weitkamp, J., et al., "Generation of recombinant human monoclonal antibodies to rotavirus from single antigen-specific B cells selected with fluorescent virus-like particles" J Immunol Meth 275(1-2):223-237 (Apr. 1, 2003).
Wrammert J., et al., "Rapid cloning of high-affinity human monoclonal antibodies against influenza virus" Nature 453(7195):667-672 (May 29, 2008).
Wu et al., "Effect of Rat Serum From Animal Treated with Qiangjijianli Fang on the Secretion of Relevant Cytokines by Thymocytes From Rat Models of Spleen-Deficiency in Vitro" J Radioimmunology—China 24(1):17-19 ( 2011).
Zhang et al., "Tumor immunosuppression and therapy" Immunology Fascicle of Foreign Medicine 24(1):50-53 ( 2001).
Zubler, R., et al., "Activated B Cells Express Receptors for, and Proliferate in Response to, Pure Interleukin 2" J Exp Med 160(4):1170-1183 (Oct. 1, 1984).
Zubler, R.,, "Polyclonal B cell responses in the presence of defined filler Cells: Complementary effects of lipopolysaccharide and anti-immunoglobulin antibodies" Eur J Immunol 14(4):357-363 (Apr. 1, 1984).

* cited by examiner

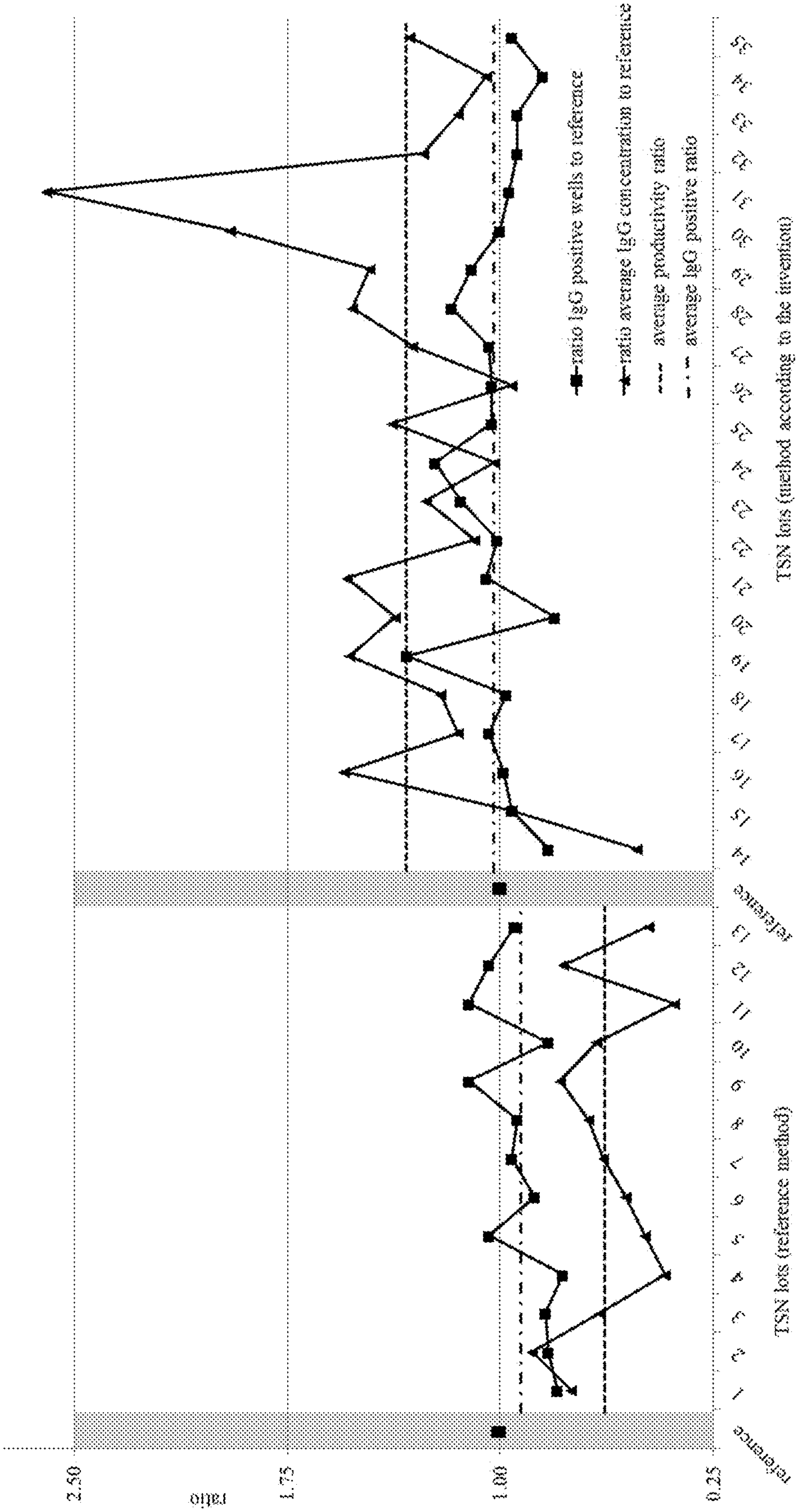
ratio
2.50
1.75
1.00
0.25
reference
TSN lots (reference method)
TSN lots (method according to the invention)
ratio IgG positive wells to reference
ratio average IgG concentration to reference
average productivity ratio
average IgG positive ratio

METHOD FOR THE PRODUCTION OF THYMOCYTE SUPERNATANT

CROSS-REFERENCE TO RELATED APPLICATION

This application is a divisional of U.S. application Ser. No. 16/591,351, filed Oct. 2, 2019, which is a continuation of PCT Application No. PCT/EP2018/062647, filed May 16, 2018, which in turn claims priority to EP Application Ser. No. 17171903.2, filed May 19, 2017, each of which is incorporated by reference herein in their entirety.

FIELD OF THE INVENTION

Herein is reported an improved method for the production of thymocyte supernatant. This supernatant can be used e.g. in co-cultivating single deposited B-cells or pools of B-cells with feeder cells.

BACKGROUND OF THE INVENTION

For obtaining cells secreting monoclonal antibodies the hybridoma technology developed by Koehler and Milstein is widely used. But in the hybridoma technology only a fraction of the B-cells obtained from an immunized experimental animal can be fused and propagated. The source of the B-cells is generally an organ of an immunized experimental animal such as the spleen.

Zubler et al. started in 1984 to develop a different approach for obtaining cells secreting monoclonal antibodies (see e.g. Eur. J. Immunol. 14 (1984) 357-63, J. Exp. Med. 160 (1984) 1170-1183). Therein the B-cells are obtained from the blood of the immunized experimental animal and co-cultivated with murine EL-4 B5 feeder cells in the presence of a cytokine comprising feeder mix.

Kwekkeboom, J., et al. (J. Immunol. Meth. 160 (1993) 117-127) reported an efficient procedure for the generation of human monoclonal antibodies based on activation of human B lymphocytes by a murine thymoma cell line. The reported that for human B-cells the cultivation conditions should be with irradiated EL4B5 in the presence of PMA (5 ng/ml) plus 5% T cells supernatant.

Weitkamp, J-H., et al., (J. Immunol. Meth. 275 (2003) 223-237) report the generation of recombinant human monoclonal antibodies to rotavirus from single antigen-specific B-cells selected with fluorescent virus-like particles.

Weber, M., et al. (J. Immunol. Meth. 278 (2003) 249-259) reported combining EL4-B5-based B-cell stimulation and phage display technology for the successful isolation of human anti-Sc1-70 autoantibody fragments.

A method of producing a plurality of isolated antibodies to a plurality of cognate antigens is reported in US 2006/0051348.

In WO 2008/144763 and WO 2008/045140 antibodies to IL-6 and uses thereof and a culture method for obtaining a clonal population of antigen-specific B cells are reported, respectively.

A culture method for obtaining a clonal population of antigen-specific B-cells is reported in US 2007/0269868.

Masri et al. (in Mol. Immunol. 44 (2007) 2101-2106) report the cloning and expression in *E. coli* of a functional Fab fragment obtained from single human lymphocyte against anthrax toxin.

A method for preparing immunoglobulin libraries is reported in WO 2007/031550.

In WO 2011/147903 a single B-cell cultivation method, wherein the co-cultivating is in the presence of a synthetic feeder mix that comprises IL-1β, TNFα, IL-10, and one or more selected from IL-21, SAC, BAFF, IL-2, IL-4, and IL-6, is reported.

In WO 2013/076139 CD40L expressing mammalian cells and their use are reported.

In U.S. Pat. No. 7,807,415 methods for producing stable immortalized B-lymphocytes are reported.

In EP 0 488 470 methods for the production of antibodies are reported.

In WO 2015/000624 co-cultivation of ovine B-cells and phorbol myristate acetate (PMA) is reported.

In WO 2012/178150 methods for developing antigen-specific antibody-producing cell lines and monoclonal antibodies are reported.

D. S. Verma et al. (Scand. J. Haem. 28 (1982) 254-263) reported about monocyte-macrophage modulation of T-lymphocyte-derived colony-stimulating activity elaboration in man.

SUMMARY OF THE INVENTION

Herein is reported an improved method for the production of thymocyte supernatant (TSN). The supernatant obtained with the inventive method can be used as additive in the co-cultivation of single deposited B-cells, which can be of any source, with feeder cells in a suitable co-cultivation medium.

TSN produced with methods known in the art shows high lot-to-lot variability. As a consequence the lots have to be characterized prior to use and low performing lots have to be discarded (or used in higher concentrations) leading to increased costs.

The invention is based at least in part on the finding that increasing the macrophage concentration during the preparation of the TSN results in a more robust production process. Additionally the TSN produced with the method according to the current invention, when used as additive in the co-cultivation of B-cells with feeder cells, results in an increased number of IgG-secreting B-cells as well as higher IgG concentrations obtained in said co-cultivations. As higher IgG concentrations are obtained, more assays to characterize the antibody secreted by the respective B-cell can be performed per cultivation.

One aspect as reported herein is a method for producing a thymocyte supernatant comprising the following steps:

- co-cultivating thymocytes and mononuclear cells (macrophages) at a cell ratio of 0.5:1.2 or more in the presence of phorbol-12-myristate-13-acetate (PMA) and phytohemagglutinin M (PHA-M) for up to 60 hours, and
- separating the co-cultivation medium from the cells and thereby producing the thymocyte supernatant.

In one embodiment the thymocyte to mononuclear cell ratio is of from 0.5:1.2 to 0.5:6 or 0.5:1.2 to 0.5:4. In one preferred embodiment the ratio is about 0.5:2.

In one embodiment the ratio is per ml of cultivation medium.

In one embodiment the thymocyte cell density is about $5\times10^5$ cells/ml ($0.5\times10^6$ cells/ml).

In one embodiment the thymocytes are obtained from the thymus of an (young) experimental animal. In one embodiment the thymocytes are T-cells.

In one embodiment prior to the co-cultivating the thymocytes are incubated for up to 60 hours at 37° C. in cultivation medium. In one embodiment this incubating is for about 30-46 hours.

In one embodiment co-cultivating thymocytes and mononuclear cells is for about 30-46 hours.

In one embodiment the mononuclear cells are isolated from the blood of an (adult) experimental animal. In one embodiment the mononuclear cells are isolated from the PBMCs of the (adult) experimental animal. In one embodiment the mononuclear cells are isolated by adherence to a solid surface from the PBMCs of the (adult) experimental animal. In one embodiment the isolation is at a cell density of $1\times10^6$ cells/ml. In one preferred embodiment the mononuclear cells are macrophages. In one embodiment the mononuclear cells are cultivation for up to 60 hours in cultivation medium prior to the co-cultivating with the thymocytes, in one embodiment for 30-48 hours.

In one embodiment prior to the co-cultivating of the thymocytes and mononuclear cells the cultivation medium of the thymocytes is replaced by fresh medium containing 10 ng/ml phorbol-12-myristate-13-acetate (PMA) and 5 μg/ml phytohemagglutinin M (PHA-M).

In one embodiment the co-cultivating is started by removing the cultivation medium from the mononuclear cells and adding the thymocyte suspension.

In one embodiment the cultivation medium of the mononuclear cells is EL4-B5 medium. In one embodiment the medium is Roswell Park Memorial Institute medium (RPMI) medium supplemented with FCS, glutamine/penicillin/streptomycin, sodium-pyruvate, 4-(2-hydroxyethyl)-1-piperazineethanesulfonic acid (HEPES) buffer and β-mercapto ethanol.

In one embodiment of all aspects the cultivating and/or the co-cultivating is in a medium comprising RPMI 1640 medium supplemented with 10% (v/v) FCS, 1% (w/v) of a 200 mM glutamine solution that comprises penicillin and streptomycin, 2% (v/v) of a 100 mM sodium pyruvate solution, and 1% (v/v) of a 1 M 2-(4-(2-hydroxyethyl)-1-piperazine)-ethane sulfonic acid (HEPES) buffer, further comprising 0.05 μM β-mercaptoethanol.

One aspect as reported herein is a method for co-cultivating one or more B-cells comprising the step of co-cultivating the one or more B-cells with EL4-B5 cells in the presence of TSN produced with a method as reported herein.

In one embodiment the co-cultivating is with *Staphylococcus aureus* strain Cowan's cells (SAC) and thymocyte cultivation supernatant produced with a method as reported herein.

In one embodiment the method is for co-cultivating one B-cell. In one preferred embodiment the one B-cell is a single deposited B-cell.

In one embodiment the co-cultivating is for 5 to 10 days.

One aspect as reported herein is a method for producing an antibody comprising a step of co-cultivating one or more B-cells with EL4-B5 feeder cells in the presence of TSN produced with the method as reported herein.

In one embodiment the method for co-cultivating one or more B-cells or for producing an antibody comprises prior to the co-cultivating step the following step:

depositing those B-cells of a population of B-cells that have been labeled with one to four fluorescence dyes/fluorophores as single cells.

The result of the co-cultivation is a B-cell clone, i.e. a population of B-cells that are the progeny of a single B-cell.

In one embodiment the population of B-cells is a non-human animal B-cell population. In one embodiment the B-cell population is a mouse B-cell population, or a hamster B-cell population, or a rabbit B-cell population. In one preferred embodiment the B-cell population is a rabbit B-cell population.

In one embodiment the B-cell population is a human B-cell population.

In one embodiment of all aspects the population of B-cells is obtained from blood by density gradient centrifugation.

In one embodiment of all aspects the B-cells are mature B-cells.

In one embodiment of all aspects the single cells are deposited (individually) into the wells of a multi-well plate.

In one embodiment the animal is an experimental animal. In one embodiment the experimental animal is selected from mouse, hamster, and rabbit. In one embodiment the experimental animal is a rabbit.

Definitions

The term "antibody" herein is used to denote naturally occurring antibodies including their naturally occurring structural variants.

For example, native (human, mouse, rat, rabbit) IgG antibodies are heterotetrameric glycoproteins with a molecular weight of about 150,000 Dalton. Native IgG antibodies are composed of two identical light chains and two identical heavy chains comprising inter- and intra-chain disulfide bonds, so that all four chains are covalently linked to each other. From N- to C-terminus, each heavy chain has a variable region (VH), also called a variable heavy chain domain or a heavy chain variable domain, followed by three constant domains (CH1, CH2, and CH3), whereby a flexible hinge region is located between the first and the second constant domain. The heavy chain of an antibody may be assigned to one of five types, called IgA, IgD, IgE, IgG and IgM, depending on their sequence and domain structure ("class" of an antibody). Several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively. Similarly, from N- to C-terminus, each light chain has a variable region (VL), also called a variable light chain domain or a light chain variable domain, followed by a constant light chain domain (CL). The light chain of an antibody may be assigned to one of two types, called kappa (κ) and lambda (λ), based on the amino acid sequence of its constant domain.

For example, native (camelid, i.e. from Camelidae, suborder Tylopoda, which includes camels, dromedaries and llamas) heavy-chain only antibodies (VHH antibodies) do not comprise a classical CH1 domain as found in conventional IgG heavy chains, and, thus, are expressed as VHH domains fused directly to the hinge-CH2-CH3 domains of an antibody. The variable region sequences from llama derived VHH antibodies, for example, are similar to sequences in the human VH3 family of variable domains (Schroeder et al., Int. Immunol. 2 (1989) 41-50). Compared to antibodies of the IgG type the CDR3 domain amino acid sequence in L. llama VHH domains is longer on average than most CDR3 domains of classical IgG type antibodies comprising heavy and light chains Alike classical IgG antibodies the position of the CDRs in VHH antibodies can be determined by methods well known in the art (see e.g.

U.S. Pat. No. 5,637,677). Residues 11, 37, 44, 45 and 47 are important for the formation of the chain interface (see e.g. WO 99/42077).

An "antibody fragment" refers to a molecule other than an intact antibodies (IgG/VHH=four chain/two chain) comprising only a portion of an intact antibody and that binds to the same antigen to which the intact antibody binds. Examples of antibody fragments include but are not limited to Fv, Fab, Fab', Fab'-SH, $F(ab')_2$; diabodies; linear antibodies; single-chain antibody molecules (e.g. scFv); single domain antibodies; and multispecific antibodies formed from antibody fragments.

The term "cell" includes both prokaryotic cells, which are used for propagation of plasmids, and eukaryotic cells, which are used for the expression of a nucleic acid. In one embodiment the eukaryotic cell is a mammalian cell. In one embodiment the mammalian cell is a CHO cell, optionally a CHO K1 cell (e.g. a ATCC CCL-61 or DSM ACC 110), or a CHO DG44 cell (also known as CHO-DHFR[−], e.g. a DSM ACC 126), or a CHO XL99 cell, a CHO-T cell (see e.g. Morgan, D., et al., Biochemistry 26 (1987) 2959-2963), or a CHO-S cell, or a Super-CHO cell (Pak, S.C.O., et al. Cytotechnol. 22 (1996) 139-146), or BHK cell, or a NSO cell, or a Sp2/0 cell, or a HEK 293 cell, or a HEK 293 EBNA cell, or a PER.C6® cell, or a COS cell. If these cells are not adapted to growth in serum-free medium or in suspension an adaptation prior to the use in the current method can be performed. As used herein, the expression "cell" includes the subject cell and its progeny. Thus, the words "transformant" and "transformed cell" include the primary subject cell and cultures derived there from without regard for the number of transfers or sub-cultivations. It is also understood that all progeny may not be precisely identical in DNA content, due to deliberate or inadvertent mutations. Variant progeny that have the same function or biological activity as screened for in the originally transformed cell are included.

The term "clone" denotes a population of dividing and antibody secreting B-cells arising from/originating from a single B-cell. Thus, a B-cell clone is a homogeneous population of B-cells and produces a monoclonal antibody.

The term "experimental animal" denotes a non-human animal. In one embodiment the experimental animal is selected from rat, mouse, hamster, rabbit, camel, llama, non-human primates, sheep, dog, cow, chicken, amphibians, sharks and reptiles. In one embodiment the experimental animal is a rabbit.

The term "expression" as used herein refers to transcription and/or translation and secretion processes occurring within a cell. The level of transcription of a nucleic acid sequence of interest in a cell can be determined on the basis of the amount of corresponding mRNA that is present in the cell. For example, mRNA transcribed from a sequence of interest can be quantified by qPCR or RT-PCR or by Northern hybridization (see Sambrook, et al., Molecular Cloning: A Laboratory Manual, Second Edition, Cold Spring Harbor Laboratory Press, Cold Spring Harbor, N.Y. (1989)). Polypeptides encoded by a nucleic acid can be quantified by various methods, e.g. by ELISA, by assaying the biological activity of the polypeptide, or by employing assays that are independent of such activity, such as Western blotting or radioimmunoas say, using immunoglobulins that recognize and bind to the polypeptide (see Sambrook, et al., (1989), supra).

To a person skilled in the art procedures and methods are well known to convert an amino acid sequence, e.g. of a polypeptide, into a corresponding nucleic acid sequence encoding this amino acid sequence and vice versa. Therefore, a nucleic acid is characterized by its nucleic acid sequence consisting of individual nucleotides and likewise by the amino acid sequence of a polypeptide encoded thereby.

An "expression cassette" denotes a construct that contains the necessary regulatory elements, such as promoter and polyadenylation site, for expression of at least the contained nucleic acid in a cell.

Expression can be performed either as transient expression or a stable expression. Antibodies are in general secreted into the cultivation medium by the cell producing it. Therefore non-mature antibody chains contain an N-terminal extension (also known as the signal sequence), which is necessary for the transport/secretion of the antibody through the cell wall into the extracellular medium. In general, the signal sequence for recombinant production of an antibody can be derived from any gene encoding a secreted polypeptide. If a heterologous signal sequence is used, it should be one that is recognized and processed (i.e. cleaved by a signal peptidase) by the host cell. For secretion in yeast for example the native signal sequence of a heterologous gene to be expressed may be substituted by a homologous yeast signal sequence derived from a secreted gene, such as the yeast invertase signal sequence, alpha-factor leader (including Saccharomyces, Kluyveromyces, Pichia, and Hansenula α-factor leaders, the second described in U.S. Pat. No. 5,010,182), acid phosphatase signal sequence, or the C. albicans glucoamylase signal sequence (EP 0 362 179). In mammalian cells the native signal sequence is satisfactory, although other mammalian signal sequences may be suitable, such as signal sequences from other secreted polypeptides of the same or related species as well as viral secretory signal sequences, for example, the herpes simplex glycoprotein D signal sequence. The DNA fragment encoding for such a pre segment is ligated in frame, i.e. operably linked, to the DNA fragment encoding an antibody chain.

The term "expression machinery" denotes the sum of the enzymes, cofactors, etc. of a cell that is involved in the steps of gene expression beginning with the transcription step of a nucleic acid or gene (i.e. also called "gene expression machinery") to the post-translational modification of the polypeptide encoded by the nucleic acid. The expression machinery e.g. comprises the steps of transcription of DNA into pre mRNA, pre-mRNA splicing to mature mRNA, translation into a polypeptide of the mRNA, and post translational modification of the polypeptide.

An "expression plasmid" or "expression vector" is a nucleic acid providing all required elements for the expression of the comprised structural gene(s) in a host cell. Typically, an expression plasmid/vector comprises a prokaryotic plasmid propagation unit, e.g. for *E. coli*, comprising an origin of replication, and a selectable marker, a eukaryotic selection marker, and one or more expression cassettes for the expression of the structural gene(s) of interest each comprising a promoter, a structural gene, optionally a transcription terminator and a polyadenylation signal. Gene expression is usually placed under the control of a promoter, and such a structural gene is said to be "operably linked to" the promoter. Similarly, a regulatory element and a core promoter are operably linked if the regulatory element modulates the activity of the core promoter.

The term "feeder mix" denotes a combination of different additives, such as growth factors, cytokines and/or further proteins promoting the activation and/or survival of B-cells and/or antibody secretion. The feeder mix is in no case herein a natural feeder mix, i.e. it is not obtained from the cultivation supernatant of thymocytes (TSN), which is a non-defined combination of cytokines. In the methods as reported herein the feeder mix if present is a synthetic feeder mix, which is a defined combination of different recombinantly produced or chemically synthesized additives, i.e. of growth factors, cytokines, interleukins and PMA, which promotes the activation and/or survival of B-cells and/or antibody secretion.

The terms "host cell", "host cell line", and "host cell culture" are used interchangeably and refer to cells into which exogenous nucleic acid has been introduced, including the progeny of such cells. Host cells include "transformants" or "transfectants" and "transformed cells" and "transfected cells", which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is an antibody, which possesses an amino acid sequence that corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

The term "labeling" denotes a process for determining the presence or absence of a surface marker, which can be determined by binding/non-binding of a specifically binding and labeled anti-surface marker antibody to a cell. Thus, the presence of a surface marker is determined e.g. in the case of a fluorescence label by the occurrence of a fluorescence whereas the absence of a surface marker is determined by the absence of a fluorescence after incubation of a cell or a population of cells with the respective specifically binding and labeled anti-surface marker antibody.

The term "monoclonal antibody" as used herein refers to an antibody obtained from a population of substantially homogeneous antibodies produced by a single cell clone, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to methods utilizing transgenic animals containing all or part of the human immunoglobulin loci, such methods and other exemplary methods for making monoclonal antibodies being described herein.

The term "PMA" denotes phorbol-12-myristate-13-acetate, a small chemical compound. The IPUAC name thereof is (1aR,1bS,4aR,7aS,7bS,8R,9R,9aS)-9a-(acetyloxy)-4a,7b-dihydroxy-3-(hydroxymethyl)-1,1,6,8-tetramethyl-5-oxo-1a,1b,4,4a,5,7a,7b,8,9,9a-decahydro-H-cyclopropa[3,4] benzo[1,2-e]azulen-9-yl myristate. This compound is also denoted as TPA, 12-O-tetradecanoylphorbol-13-acetate, tetradecanoylphorbol acetate, tetradecanoyl phorbol acetate, phorbol myristate acetate, 12-O-tetradecanoylphorbol 13-acetate, 12-tetradecanoylphorbol 13-acetate, 12-tetradecanoylphorbol 13-monoacetate, 13-O-acetylphorbol 12-myristate, 4β-phorbol 12-myristate 13-acetate, myristic acid, 9-ester with 1,1aα,1bβ, 4,4a,7aα,7b,8,9,9a-decahydro-4aβ, 7bα,9β,9aα-tetrahydroxy-3-(hydroxymethyl)-1,1,6,8α-tetramethyl-5H-cyclopropa[3,4]benz[1,2-e]azulen-5-one 9a-acetate, (+)-, phorbol 12-myristate 13-acetate, phorbol 12-tetradecanoate 13-acetate, phorbol myristate acetate, PMA, PMA (tumor promoter), tetradecanoic acid, (1aR,1bS,4aR,7aS,7bS,8R,9R,9aS)-9a-(acetyloxy)-1a, 1b,4,4a,5,7a,7b,8,9,9a-decahydro-4a,7bdihydroxy-3-(hydroxymethyl)-1,1,6,8-tetramethyl-5-oxo-1H-cyclopropa[3,4]benz [1,2-e]azulen-9-yl ester, tetradecanoic acid, 9a-(acetyloxy)-1a,1b,4,4a,5,7a,7b,8,9,9a-decahydro-4a,7b-dihydroxy-3-(hydroxymethyl)-1,1,6,8-tetramethyl-5-oxo-1H-cyclopropa [3,4]benz[1,2-e]azulen-9-yl ester, [1aR(1aα,1bβ,4aβ,7aaα, 7bα,8α,9β,9aα)]-, TPA and TPA (phorbol derivative).

A "transfection plasmid/vector" is a nucleic acid (also denoted as nucleic acid molecule) providing all required elements for the expression of the in the transfection plasmid/vector comprised coding nucleic acids/structural gene (s) in a host cell. A transfection plasmid/vector comprises a prokaryotic plasmid propagation unit, e.g. for *E. coli*, in turn comprising a prokaryotic origin of replication, and a nucleic acid conferring resistance to a prokaryotic selection agent, further comprises the transfection plasmid/vector one or more nucleic acid(s) conferring resistance to an eukaryotic selection agent, and one or more nucleic acid encoding a polypeptide of interest. The nucleic acids conferring resistance to a selection agent and the nucleic acid(s) encoding a polypeptide of interest are placed each within an expression cassette, whereby each expression cassette comprises a promoter, a coding nucleic acid, and a transcription terminator including a polyadenylation signal. Gene expression is usually placed under the control of a promoter, and such a structural gene is said to be "operably linked to" the promoter. Similarly, a regulatory element and a core promoter are operably linked if the regulatory element modulates the activity of the core promoter.

The term "variable region" or "variable domain" refers to the region of an antibody heavy or light chain that is involved in the binding of the antibody to its antigen. The variable domains of the heavy chain and light chain (VH and VL, respectively) of a native antibody generally have similar structures, with each domain comprising four conserved framework regions (FRs) and three hypervariable regions (HVRs) (see, e.g., Kindt, T. J., et al., Kuby Immunology, 6th ed., W. H. Freeman and Co., N.Y. (2007), page 91). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively (see, e.g., Portolano, S., et al., J. Immunol. 150 (1993) 880-887; Clackson, T., et al., Nature 352 (1991) 624-628).

The term "young animal" denotes an animal before sexual maturity occurs. A young hamster, for example, is of an age of less than 6 weeks, especially less than 4 weeks. A young mouse, for example, is of an age of less than 8 weeks, especially less than 5 weeks. A young rabbit is of an age of less than 8 weeks, especially about 5 weeks.

The term "Roswell Park Memorial Institute medium (RPMI)" denotes a medium with the following composition:

Components in [mg/L] in final medium:

| Inorganic salts | |
|---|---|
| calcium chloride × 2H2O | 62.27 |
| potassium chloride | 400 |
| magnesium sulfate, dried | 69.77 |
| sodium chloride | 5950.49 |
| sodium nitrate | 72 |
| di-sodium hydrogen phosphate anhydr. | 800 |

| Other Components | |
|---|---|
| D(+)-Glucose anhydr. | 2000 |
| L-glutathione red. | 1 |

| Amino acids | |
|---|---|
| L-arginine × HCl | 241.86 |
| L-asparagine × H2O | 50 |
| L-aspartic acid | 20 |
| L-cystine | 50 |
| L-glutamic acid | 20 |
| glycine | 10 |
| L-histidine base | 15 |
| L-hydroxyproline | 20 |
| L-isoleucine | 50 |
| L-leucine | 50 |
| L-lysine × HCl | 40 |
| L-methionine | 15 |
| L-phenylalanine | 15 |
| L-proline | 20 |
| L-serine | 30 |
| L-threonine | 20 |
| L-tryptophan | 5 |
| L-tyrosine | 20 |
| L-valine | 20 |

| Vitamins | |
|---|---|
| 4-amino benzoic acid | 1 |
| D(+)-biotin | 0.2 |
| D-calcium pantothenate | 0.25 |
| choline chloride | 3 |
| folic acid | 1 |
| myo-inositol | 35 |
| nicotinamide | 1 |
| pyridoxine × HCl | 1 |
| riboflavin | 0.2 |
| thiamine × HCl | 1 |
| vitamin B12 | 0.005 |

In one embodiment the cultivation medium of the mononuclear cells is modified Roswell Park Memorial Institute medium (RPMI) medium wherein to each 450 ml RPMI medium are added 50 ml fetal calf serum (FCS), 5 ml glutamine/penicillin/streptomycin mix (100×; 10.000 units penicillin, 10.000 μg streptomycin and 29.2 mg/ml L-glutamine in 10 mM citrate buffer), 10 ml sodium pyruvate solution, 5 ml 1 M HEPES buffer, 500 μl (50 mM) β-mercaptoethanol.

DETAILED DESCRIPTION

In the following the invention is exemplified using rabbit B-cells. This is an example and shall not be construed as a limitation. The invention can be practised with B-cells of any origin.

A. The Production of TSN Prior to the Current Invention

Rabbit specific cytokines were generated by the preparation of a rabbit thymocyte supernatant (TSN). Therefore rabbit T-cells and rabbit macrophages were used (see e.g. Weber, M., et al., J. Immunol. Meth. (2003); Steenbakkers, P. G., et al., Mol. Biol. Rep. (1994)). The rabbit T-cell precursors can be isolated from the thymus of 4-5 week-old rabbits (see e.g. WO 2011/147903; Seeber, S., et al., PLoS ONE (2014) e86184).

Briefly, the thymocytes are seeded at a cell density of $5\times10^5$ cells/ml in cell culture flasks in a cultivation medium and incubated for about 48 h, at 37° C. PBMCs isolated from blood of adult rabbits are used to enrich monocytes/macrophages by adherence at 37° C. in cultivation medium at a cell density of 1-$3\times10^6$ cells/ml. Attached monocytes/macrophages are cultivated for about 48 h in a cultivation medium. T-cells and macrophages obtained from different rabbits are kept in separate flasks. Prior to the mixing of T-cells and macrophages, T-cells are centrifuged and resuspended in cultivation medium containing 10 ng/ml phorbol-12-myristate-13-acetate (PMA) and 5 μg/ml phytohemagglutinin M (PHA-M) at a cell density of $5\times10^5$ cells/ml. The medium is removed from the macrophage cultures and replaced by the T-cell suspension to have a final macrophage concentration of $1\times10^6$ cells/ml. After co-cultivation for 48 hours, the T-cell/macrophage conditioned medium is removed and termed (TSN).

In the following Table 1 the characteristics of TSN lots produced with the method as outlined above is shown (see also FIG. 1, left part; obtained with method according to example 12 using a TSN produced with a method according to example 10).

TABLE 1

| TSN lot | ratio IgG positive wells to reference | ratio average productivity wells to reference |
|---|---|---|
| reference | 1.00 | 1.00 |
| 1 | 0.80 | 0.75 |
| 2 | 0.83 | 0.89 |
| 3 | 0.84 | 0.65 |
| 4 | 0.78 | 0.42 |
| 5 | 1.04 | 0.49 |
| 6 | 0.88 | 0.56 |
| 7 | 0.96 | 0.64 |
| 8 | 0.94 | 0.69 |
| 9 | 1.11 | 0.79 |
| 10 | 0.83 | 0.66 |
| 11 | 1.11 | 0.39 |
| 12 | 1.04 | 0.78 |
| 13 | 0.95 | 0.48 |
| average | 0.93 | 0.63 |

Thus, TSN lots produced with the method as known from the art show a high lot to lot variability. As a consequence low performing TSN lots have to be identified and discarded or added in higher amounts in a B-cell co-cultivation, both leading, amongst other things, to increased costs.

B. The Production of TSN with Novel and Inventive Method as Reported Herein

Herein is reported an improved method for the production of thymocyte supernatant (TSN). The TSN produced with the method as reported herein can be used as additive in the co-cultivation of single deposited B-cells, which can be of any source, with feeder cells in a suitable co-cultivation medium.

The invention is based at least in part on the finding that the increase of the macrophage to T-cell ratio during the preparation of the TSN leads to a TSN preparation that, when used as additive in the co-cultivation of B-cells and feeder cells, results in higher overall IgG-concentrations. This, in turn, results in the beneficial effect that more assays can be performed per cultivation supernatant. In addition, this improvement reduces the discharge rate of the TSN lots.

One aspect as reported herein is a method for producing a thymocyte supernatant comprising the following steps:

co-cultivating thymocytes and mononuclear cells at a cell ratio of 0.5:1.2 or more in the presence of phorbol-12-myristate-13-acetate (PMA) and phytohemagglutinin M (PHA-M) for up to 60 hours, and separating the co-cultivation medium from the cells and thereby producing the thymocyte supernatant.

In one embodiment the thymocyte to mononuclear cell ratio is of from 0.5:1.2 to 0.5:4. In one embodiment the ratio is of from 0.5:1.5 to 0.5:3. In one preferred embodiment the ratio is about 0.5:2.

In one embodiment the thymocyte cell density is about $5\times10^5$ cells/ml ($0.5\times10^6$ cells/ml).

In one embodiment the thymocytes are obtained from the thymus of an (young) experimental animal. In one embodiment the thymocytes are T-cells.

In one embodiment prior to the co-cultivating the thymocytes are incubated for up to 60 hours at 37° C. in cultivation medium. In one embodiment this incubating is for about 30-46 hours. In one preferred embodiment for about 40 hours.

In one embodiment the mononuclear cells are isolated from the blood of an (adult) experimental animal. In one embodiment the mononuclear cells are isolated from the PBMCs of the (adult) experimental animal. In one embodiment the mononuclear cells are isolated by adherence to a solid surface from the PBMCs of the (adult) experimental animal. In one embodiment the isolation is at a cell density of $1\text{-}3\times10^6$ cells/ml, in one preferred embodiment of about $2\times10^6$ cells/ml. In one preferred embodiment the attached mononuclear cells are macrophages. In one embodiment the attached mononuclear cells are cultivation for up to 60 hours in cultivation medium prior to the co-cultivating with the thymocytes, in one preferred embodiment for about 40-48 hours.

In one embodiment prior to the co-cultivating of the thymocytes and mononuclear cells the cultivation medium of the thymocytes is replaced by fresh medium containing 10 ng/ml phorbol-12-myristate-13-acetate (PMA) and 5 μg/ml phytohemagglutinin M (PHA-M).

In one embodiment the co-cultivating is started by removing the cultivation medium from the mononuclear cells and adding the thymocyte suspension.

In one embodiment the cultivation medium of the mononuclear cells is EL4-B5 medium. In one embodiment the medium is RPMI 1640 medium supplemented with FCS, glutamine/penicillin/streptomycin, Na-pyruvate, HEPES buffer and beta-mercapto ethanol.

It has been found that depending on the amount of macrophages present in the co-cultivation of thymocytes (T-cells) with mononuclear cells (macrophages), i.e. depending on the ratio of said cells, the produced TSN shows different properties. The respective results are shown in the following Table 2 (total wells=4*84).

TABLE 2

| ratio [*$10^6$ cells/ml] thymocytes:mononuclear cells | average IgG positive wells [n] | average frequency of IgG positive wells [% of total wells] | average productivity of all IgG positive wells [μg/ml] |
|---|---|---|---|
| 0.5:1 | 33.3 ± 2.3 | 39.6 ± 2.7 | 0.35 ± 0.05 |
| 0.5:1.25 | 38.8 ± 4.8 | 46.1 ± 5.7 | 0.81 ± 0.10 |
| 0.5:1.5 | 34.5 ± 5.5 | 41.1 ± 6.6 | 1.22 ± 0.12 |
| 0.5:2 | 37.3 ± 1.8 | 44.4 ± 2.1 | 1.32 ± 0.23 |

In the following Table 3 the characteristics of TSN lots produced with the method according to the current invention as reported herein is shown (see also FIG. 1, right part; obtained with single deposited B-cells according to Example 12 using a TSN produced with a method according to Example 9).

TABLE 3

| TSN lot | ratio IgG positive wells to reference | ratio average productivity wells to reference |
|---|---|---|
| reference | 1.00 | 1.00 |
| 14 | 0.83 | 0.52 |
| 15 | 0.96 | 0.96 |
| 16 | 0.99 | 1.55 |
| 17 | 1.04 | 1.15 |
| 18 | 0.98 | 1.21 |
| 19 | 1.33 | 1.53 |
| 20 | 0.81 | 1.37 |
| 21 | 1.05 | 1.54 |
| 22 | 1.01 | 1.09 |
| 23 | 1.14 | 1.26 |
| 24 | 1.23 | 1.02 |
| 25 | 1.03 | 1.38 |
| 26 | 1.03 | 0.96 |
| 27 | 1.04 | 1.31 |
| 28 | 1.17 | 1.52 |
| 29 | 1.10 | 1.46 |
| 30 | 1.00 | 1.95 |
| 31 | 0.97 | 2.60 |
| 32 | 0.94 | 1.27 |
| 33 | 0.94 | 1.15 |
| 34 | 0.85 | 1.05 |
| 35 | 0.96 | 1.32 |
| average | 1.02 | 1.33 |

Thus, TSN lots produced with the inventive method as reported herein show a reduced lot to lot variability. Additionally the secreted IgG concentration in the cultivation supernatant is increased.

C. B-Cell Cloning Process using TSN Produced with the Inventive Method as Reported Herein Immunization For the generation of therapeutic antibodies either a non-human animal is immunized with the therapeutic target (either alone or in combination with an immunogenic stimulus) to elicit an immune response or synthetic approaches, such as phage display libraries are used. If a transgenic animal (i.e. having a human immune system) or a human phage display library is used human antibodies are obtained. Otherwise non-human animal antibodies are obtained that will be humanized thereafter. A rare possibility to obtain potential therapeutic antibodies is from the blood of a human being that has recovered from a disease.

Often non-human animals, such as mice, rabbits, hamster and rats, are used as animal model for evaluating antibody based therapies. Therefore, it is normally required to provide cross-reactive antibodies binding to the non-human animal antigen as well as to the human antigen.

In the methods as reported herein B-cells obtained from any source e.g. in one embodiment one or more human, mouse, hamster or rabbit B-cells, can be used.

In case of a rabbit B-cell the feeder cells can be either murine EL4-B5 cells or a mammalian cells, such as CHO cells or BHK cells or HEK cells, expressing rabbit CD40L. In one embodiment the rabbit is selected from the group consisting of New Zealand White (NZW) rabbits, Zimmermann-rabbits (ZIKA), Alicia-mutant strain rabbits, basilea mutant strain rabbits, transgenic rabbits with a human immunoglobulin locus, rbIgM knock-out rabbits, and cross-breeding thereof.

In case of a human B-cell the feeder cells can be either murine EL4-B5 cells or mammalian cells, such as CHO cells or BHK cells or HEK cells, expressing human CD40L.

In case of a murine B-cell the feeder cells can be either murine EL4-B5 cells or mammalian cells, such as CHO cells or BHK cells or HEK cells, expressing mouse CD40L. In one embodiment the mouse is an NMRI-mouse or a balb/c-mouse.

In case of a hamster B-cell the feeder cells can be either murine EL4-B5 cells or mammalian cells, such as CHO cells or BHK cells or HEK cells, expressing hamster CD40L. In one embodiment the hamster is selected from the group consisting of Armenian hamster (Cricetulus migratorius), Chinese hamster (Cricetulus griseus), and Syrian hamster (Mesocricetulus auratus). In one embodiment the hamster is the Armenia hamster.

In one embodiment the non-human animals, e.g. mice, hamster and rabbits, chosen for immunization are not older than 12 weeks.

Source and Isolation of B-Cells

Blood provides a high diversity of antibody producing B-cells. The therefrom obtained B-cell clones secrete antibodies that have almost no identical or overlapping amino acid sequences within the CDRs, thus, show a high diversity.

In one embodiment B-cells, e.g. from the blood, are obtained of from 4 days after immunization until at most 9 days after immunization or the most recent boost of the non-human animal. This time span allows for a high flexibility in the method as reported herein. In this time span it is likely that the B-cells providing for the most affine antibodies migrate from spleen to blood (see e.g. Paus, D., et al., JEM 203 (2006) 1081-1091; Smith, K. G. S., et al., The EMBO J. 16 (1997) 2996-3006; Wrammert, J., et al., Nature 453 (2008) 667-672).

B-cells from the blood, e.g. of a non-human animal or from human blood, may be obtained with any method known in the art. For example, density gradient centrifugation (DGC) or red blood cell lysis (lysis) can be used. Density gradient centrifugation compared to hypotonic lysis provides for a higher overall yield, i.e. number of B-cell clones. Additionally from the cells obtained by density gradient centrifugation a larger number of cells divide and grow in the co-cultivation step. Also the concentration of secreted antibody is higher compared to cells obtained with a different method. Therefore, in one embodiment the providing of a population of B-cells is by density gradient centrifugation.

Selection Steps Prior to Co-Cultivation

B-cells producing antibodies that specifically bind an antigen can be enriched, e.g. from peripheral blood mononuclear cells (PBMCs). Thus, in one embodiment of all methods as reported herein the B-cell population is enriched from peripheral blood mononuclear cells (PBMCs).

In one embodiment of all methods as reported herein the PBMCs are depleted of macrophages. This is advantageous for B-cells of rabbit origin for the co-cultivation step. Macrophages can be depleted from PBMCs by adhesion to the surface of the cell culture plate.

In one embodiment of the methods as reported herein the B-cells are from a protein-immunized animal and are depleted of macrophages prior to labeling.

Cells not producing an antibody binding the antigen or, likewise, cells producing an antibody binding to the antigen can be reduced or enriched, respectively, by using a panning approach. In panning the respective antigen is presented attached to a surface and cells binding thereto can be selectively enriched in/from a cell population (in this case the cells bound to the surface attached antigen are processed further).

The method as reported herein comprises in one embodiment prior to the single cell depositing a selecting step in which B-cells producing specific and/or non-cross-reactive antibodies are selected based on cell surface markers and fluorescence activated cell sorting/gating. In one embodiment mature B-cells are sorted/enriched/selected. For selection of B-cells from different non-human animal species different cell surface markers can be used.

With the labeling of non-target cell populations and non-specifically binding lymphocytes it is possible to selectively deplete these cells. In such a depletion step only a partial depletion can be achieved. Albeit the depletion is not quantitative it provides for an advantage in the succeeding fluorescence labeling of the remaining cells as the number of interfering cells is reduced. By performing a single cell depositing of mature B-cells (memory B-cells, affinity matured plasmablasts and plasma cells) using fluorescence activated cell sorting a higher number of $IgG^+$-wells/number of single deposited cells can be obtained in the co-cultivation step.

Different cell populations can be labeled specifically by using different surface markers such as e.g. $CD3^+$-cells (T-cells), $CD19^+$-cells (B-cells), $IgM^+$-cells (mature naive B-cells), $IgG^+$-cells (mature B-cells), CD38k-cells (e.g. plasmablasts), and $IgG^+CD38^+$-cells (pre-plasma cells).

Immuno-fluorescence labeling for selection of mature $IgG^+$-B-cells, such as memory B-cells, plasmablasts, and plasma cells, is available. For a selection or enrichment of B-cells the cells are either single labeled, or double labeled, or triple labeled. Also advantageous is a labeling that results in a fraction of about 0.1% to 2.5% of labeled cells with respect to the total cell population.

In one embodiment B-cells are deposited as single cells selected by the labeling of surface molecules present on 0.1% to 2.5% of the B-cells in the population, in another embodiment on 0.3% to 1.5% of the B-cells of the population, in a further embodiment on 0.5% to 1% of the B-cells of the population.

In one embodiment the method is with the proviso that if the cells are of rabbit origin the labeling is not of $IgG^+$-B-cells and/or $CD138^+$-B-cells.

In one embodiment of all methods as reported herein $IgG^+CD19^+$-B-cells are deposited as single cells from the B-cells obtained from a non-immunized non-human animal or from a human.

TABLE 4

Immuno-fluorescence labeling for the determination of mature mouse-(A-J), hamster-(K) and rabbit (L-N)-B-cells.

| B-cell origin | sorting of B-cells with | fraction of all viable cells (%) |
|---|---|---|
| mouse | $IgG^+CD19^+$ | 0.5 ± 0.2 n = 14 |
| mouse | $IgG^+CD38^+$ | 0.8 ± 0.5 n = 9 |
| mouse | $IgG^+CD138^+$ | 0.06 ± 0.07 n = 6 |
| mouse | $IgG^-CD138^+$ | 0.6 ± 0.5 n = 6 |
| mouse | $IgG^+CD27^+$ | 0.1 ± 0.1 n = 8 |
| mouse | $CD27^+CD138^+$ | 1.5 ± 0.5 n = 2 |
| mouse | $CD27^+IgG^+CD3^-$ | 0.10 ± 0.04 n = 3 |
| mouse | $CD3^-CD27^+$ | 1.33 n = 1 |
| mouse | $IgG^+CD268^+$ | 0.8 n = 1 |
| mouse | $CD38^+CD3^-$ | 12 ± 7 n = 2 |
| hamster | $IgG^+IgM^-$ | 0.6 ± 0.1 n = 15 |
| rabbit | $IgG^+$ | 0.6 ± 0.2, n = 5 |
| rabbit | $IgG^+IgM^-$ | 0.4 ± 0.2, n = 2 |
| rabbit | $IgG^+CD138^+$ | 0.3 ± 0.1, n = 5 |

In one embodiment the methods comprise the step of depleting the B-cell population of macrophages and enriching of B-cells of the B-cell population secreting antibody specifically binding a target antigen.

In one embodiment of all aspects the population of B-cells is a non-human animal B-cell population. In one embodiment the B-cell population is a mouse B-cell population, or a hamster B-cell population, or a rabbit B-cell population. In one preferred embodiment the B-cell population is a rabbit B-cell population.

In one embodiment the B-cell population is a human B-cell population.

In one embodiment of all aspects the B-cells are mature B-cells.

In one embodiment of all aspects the single cells are deposited (individually) into the wells of a multi-well plate.

In one embodiment of all aspects the deposited cells are labeled with one or three fluorescence dyes and the incubation is with two to four fluorescently labeled antibodies.

In one embodiment of all aspects the labeling of the B-cells of the population of B-cells results in labeling of 0.1% to 2.5% of the cells of the (total) B-cell population.

In one embodiment of all aspects the labeling is of B-cell surface IgG.

In one embodiment of all aspects the incubation is with a fluorescently labeled anti-IgG antibody and a fluorescently labeled anti-IgM antibody (the labeling is of cell surface IgG and cell surface IgM) and the selection is of cells positive for cell surface IgG and negative for cell surface IgM (results in single cell deposition of IgG+IgM−-B-cells).

In one embodiment of all aspects the incubation is with a fluorescently labeled anti-IgG antibody and a fluorescently labeled anti-light chain antibody (the labeling is of cell surface IgG and cell surface antibody light chain) and the selection is of cells positive for cell surface IgG and positive for cell surface antibody light chain (results in single cell deposition of IgG+LC+-B-cells).

In one embodiment of all aspects the incubation is with a fluorescently labeled anti-IgG antibody and a fluorescently labeled anti-IgM antibody (the labeling is of cell surface IgG and cell surface IgM) and the selection is of cells positive for cell surface IgG and negative for cell surface IgM (results in single cell deposition of IgG+IgM−-B-cells), whereby the population of B-cells has been incubated with (target) antigen, which is immobilized on a solid surface, and (only) B-cells bound to the immobilized antigen have been recovered and subjected to the incubation with the fluorescently labeled antibodies.

In one embodiment of all aspects the incubation is with a fluorescently labeled anti-IgG antibody and a fluorescently labeled anti-CD19 antibody (the labeling is of cell surface IgG and cell surface CD19) and the selection is of cells positive for cell surface IgG and also positive for cell surface CD19 (results in single cell deposition of IgG+CD19+-B-cells).

In one embodiment of all aspects the incubation is with a fluorescently labeled anti-IgG antibody and a fluorescently labeled anti-CD38 antibody (the labeling is of cell surface IgG and cell surface CD38) and the selection is of cells positive for cell surface IgG and also positive for cell surface CD38 (results in single cell deposition of IgG+CD38+-B-cells).

In one embodiment of all previous embodiment the incubation is in addition with a fluorescently labeled anti-light chain antibody (the labeling is of cell surface antibody light chain in addition to the other two labels) and the selection is of cells positive for cell surface antibody light chain (results in single cell deposition of LC+-B-cells).

In one embodiment of all aspects the B-cell population is a rabbit B-cell population and the incubation is with a fluorescently labeled anti-IgG antibody (the labeling is of cell surface IgG) and the selection is of cells positive for cell surface IgG (results in single cell deposition of IgG+-B-cells).

In one preferred embodiment of all aspects the B-cell population is a rabbit B-cell population and the incubation is with a fluorescently labeled anti-IgG antibody and a fluorescently labeled anti-IgM antibody (the labeling is of cell surface IgG and cell surface IgM) and the selection is of cells positive for cell surface IgG and negative for cell surface IgM (results in single cell deposition of IgG+IgM−-B-cells).

In one embodiment of all previous embodiment the incubation of the rabbit B-cells is in addition with a fluorescently labeled anti-light chain antibody (the labeling is of cell surface antibody light chain in addition to the other two labels) and the selection is of cells positive for cell surface antibody light chain (results in single cell deposition of LC+-B-cells).

In one embodiment of all aspects the B-cell population is a hamster B-cell population and the incubation is with a fluorescently labeled anti-IgG antibody and a fluorescently labeled anti-IgM antibody (the labeling is of cell surface IgG and cell surface IgM) and the selection is of cells positive for cell surface IgG and negative for cell surface IgM (results in single cell deposition of IgG+IgM−-B-cells).

In one embodiment of all aspects the B-cell population is a murine B-cell population and the incubation is with a fluorescently labeled anti-IgG antibody (the labeling is of cell surface IgG) and the selection is of cells positive for cell surface IgG (results in single cell deposition of IgG+-B-cells).

In one embodiment of all aspects the B-cell population is a murine B-cell population and the incubation is with a fluorescently labeled anti-IgG antibody and a fluorescently labeled anti-CD19 antibody (the labeling is of cell surface IgG and cell surface CD19) and the selection is of cells positive for cell surface IgG and also positive for cell surface CD19 (results in single cell deposition of IgG+CD19+-B-cells).

In one embodiment the animal is an experimental animal. In one embodiment the experimental animal is selected from mouse, hamster, and rabbit. In one embodiment the experimental animal is a rabbit.

Single Cell Depositing

The method as reported herein comprises the step of depositing the B-cells of a B-cell population as single cells. In one embodiment of all methods as reported herein the depositing as single cells is by fluorescence activated cell sorting (FACS). The surface marker used for the labeling required for the FACS single cell depositing can be with the specific marker combination as outlined herein.

The depositing is by introducing the labeled B-cell preparation into a flow cytometer and depositing those cells as single cells that have been labeled with one to three fluorescent labels. As it is possible to incubate the cells with more fluorescent dyes as those which are used for selecting the cells in the cell sorter the cells can be selected for the presence of specific surface markers and (optionally) simultaneously for the absence of other surface markers.

The labeling and single cell deposition is done in order to reduce the complexity of the B-cell population by depleting those B-cells that are not likely to produce an antibody having the intended characteristics. The labeled antibodies bind to a specific polypeptide displayed on the surface of B-cells and, thus, provide for a positive selection label. Likewise it is also possible to select cells that are only labeled with a reduced number of fluorescent dyes compared to the number of labeled antibodies with which the B-cell had been incubated, such as e.g. cells having one fluorescent label out of two (i.e. incubation with two fluorescently label antibodies has been performed but only one thereof binds to the B-cells). Based on the binding/non-binding of the fluorescently labeled antibodies to the individual B-cells of the B-cell population it is possible to identify and separate target B-cells using a microfluidic sorting apparatus. Concomitantly with the selection also the amount of the label can be determined.

An additional centrifugation step after the single cell depositing and prior to the co-cultivation can increase the number of antibody secreting cells and the amount of the secreted IgG.

In one embodiment of all methods as reported herein the method comprises the step of centrifuging the single deposited cells prior to the co-cultivation with feeder cells. In one preferred embodiment the centrifuging is for 5 min. at 300×g.

Co-Cultivation

Single deposited B-cells can be co-cultivated with feeder cells in the presence of TSN produced with a method as reported herein as additive. In one embodiment the B-cells are co-cultivated with murine EL-4 B5 cells as feeder cells.

The co-cultivation step with feeder cells can be preceded and also succeeded by a number of additional steps.

By using the TSN produced with a method as reported herein after about seven (7) days, i.e. after 5, 6, 7, or 8 days, especially after 7 or 8 days, of co-cultivation high antibody concentrations in the cultivation supernatant can be obtained. With the thereby provided amount of antibody a high number of different analyses can be performed in order to characterize the antibody, e.g. regarding binding specificity, in more detail. With the improved characterization of the antibody at this early stage in the screening/selection process it is possible to reduce the number of required nucleic acid isolations and sequencing reactions that have to be performed. Additionally the B-cell clone provides an amount of mRNA encoding monoclonal light and heavy chain variable region allowing the use of degenerated PCR primer and obviates the requirement of highly specific primer. Also the required number of PCR cycles is reduced. Thus, in one embodiment the reverse transcriptase PCR is with degenerated PCR primer for the light and heavy chain variable domain.

In one embodiment of all B-cell co-cultivation methods as reported herein the thymocyte cultivation supernatant is obtained with a method as reported herein.

Characterization of Co-Cultivated Cells

For the (qualitative and quantitative) determination of secreted IgG after the co-cultivation generally all methods known to a person of skill in the art such as an ELISA can be used. In one embodiment of all methods as reported herein an ELISA is used.

Depending on the characterization results a B-cell clone can be obtained, i.e. selected. The term “clone” denotes a population of dividing and antibody secreting B-cells arising from/originating from a single B-cell. Thus, a B-cell clone produces a monoclonal antibody.

Further Methods Using the Method as Reported Herein:

One aspect as reported herein is a method for co-cultivating one or more B-cells (for the production of immunoglobulin) comprising the step of co-cultivating the one or more B-cells with feeder cells in the presence TSN produced with a method as reported herein (and thereby producing immunoglobulin).

In one embodiment the method further comprises the step of recovering the immunoglobulin from the cells or the cultivation medium and thereby producing the immunoglobulin.

In one embodiment the immunoglobulin is an antibody.

In one embodiment the co-cultivating is further in the presence of 1.5-7.25 ng/ml phorbol myristate acetate.

In one embodiment the co-cultivating is further in the presence of *Staphylococcus aureus* strain Cowan’s cells (SAC).

In one embodiment the feeder cells are (murine) EL4-B5 cells.

In one embodiment the method is for the co-cultivation of one B-cell. In one preferred embodiment the one B-cell is a single deposited B-cell.

In one embodiment the co-cultivating is for 5 to 14 days.

The result of the co-cultivating is a B-cell clone, i.e. a population of B-cells that are the progeny of a single B-cell.

In one embodiment the method for co-cultivating one or more B-cells comprises prior to the co-cultivating step the following step:

depositing those B-cells of a population of B-cells that have been labeled with one to three fluorescence dyes/fluorophores as single cells.

In one embodiment the method for co-cultivating one or more B-cells comprises prior to the co-cultivating step the following step:

depositing those B-cells of a population of B-cells as single cells that have been contacted with two to four antibodies each specifically binding to a different B-cell surface antigen, whereby each antibody is conjugated to a different fluorescent dye, but labeled only with one to three fluorescence dyes.

The labeling is in one embodiment by contacting the B-cell population (sequentially or simultaneously) with two to four fluorescently labeled antibodies.

In one embodiment the method for co-cultivating one or more B-cells comprises the step of incubating the population of B-cells in the co-cultivation medium prior to the single cell depositing/deposition. In one embodiment the incubating is at about 37° C. In one embodiment the incubating is for 0.5 to two hours.

In one embodiment the incubating is for about one hour. In one preferred embodiment the incubating is at about 37° C. for about one hour.

In one embodiment the method for co-cultivating one or more B-cells comprises after the depositing step and before the co-cultivating step the step of centrifuging the single cell deposited B-cells. In one embodiment the centrifuging is for about 1 min. to about 30 min. In one embodiment the centrifuging is for about 5 min. In one embodiment the centrifuging is at about 100×g to about 1,000×g. In one embodiment the centrifuging is at about 300×g. In one preferred embodiment the centrifuging is for about 5 min. at about 300×g.

In one embodiment the method for co-cultivating one or more B-cells comprises the following steps as first steps a) labeling the B-cells of a population of B-cells with one to three fluorescent dyes (optionally by incubating the B-cell population with two to four fluorescently labeled antibodies specifically binding to two to four different pre-determined B-cell surface markers),
b) optionally incubating the cells in co-cultivation medium,
c) depositing those B-cells of the population of B-cells that have been labeled with one to three fluorescent dyes (and optionally not labeled with the other fluorescent dye(s)) as single cells,
d) optionally centrifuging the single deposited B-cells,
e) (individually) co-cultivating each single deposited B-cell with feeder cells in a co-cultivation medium, which has been supplemented with a feeder mix,
f) selecting a B-cell clone proliferating and secreting an antibody in step e).

One aspect as reported herein is a method for producing an antibody comprising the following steps:

a) labeling the B-cells of a population of B-cells with one to three fluorescent dyes (optionally by incubating the B-cell population with two to four fluorescently labeled antibodies specifically binding to two to four different pre-determined B-cell surface markers),
b) optionally incubating the cells in co-cultivation medium,
c) depositing those B-cells of the population of B-cells that have been labeled with one to three fluorescent dyes (and optionally not labeled with the other fluorescent dye(s)) as single cells,
d) optionally centrifuging the single deposited B-cells,
e) (individually) co-cultivating each single deposited B-cell with feeder cells in a co-cultivation medium, which has been supplemented with a feeder mix,
f) selecting a B-cell clone of step e) secreting an antibody,
g) i) obtaining one or more nucleic acids encoding the secreted antibody's variable domains from the B-cell clone selected in step f), ii) if the B-cell clone is not a human B-cell clone humanizing the variable domains and providing the respective encoding nucleic acids, and iii) introducing the one or more nucleic acids in one or more expression vectors,
h) cultivating a cell, which has been transfected with the one or more expression vectors of step g), and recovering the antibody from the cell or the cultivation supernatant and thereby producing the antibody.

In one embodiment the method for producing an antibody comprises the following steps a) labeling the B-cells of a population of B-cells with one to three fluorescent dyes (optionally by incubating the B-cell population with two to four fluorescently labeled antibodies specifically binding to two to four different pre-determined B-cell surface markers),
b) optionally incubating the cells in co-cultivation medium,
c) depositing those B-cells of a population of B-cells that have been labeled with one to three fluorescent dyes (and optionally not labeled with the other fluorescent dye(s)) as single cells,
d) optionally centrifuging the single deposited B-cells,
e) (individually) co-cultivating each single deposited B-cell with feeder cells in a co-cultivation medium, which has been supplemented with a feeder mix,
f) determining the binding specificity of the antibodies secreted in the cultivation medium of the individual B-cells,
g) obtaining one or more nucleic acids encoding the secreted antibody's variable domains from the B-cell clone by a reverse transcriptase PCR and nucleotide sequencing, (and thereby obtaining a monoclonal antibody variable light and heavy chain domain encoding nucleic acid,)
h) if the B-cell is a non-human B-cell humanizing the variable light and heavy chain domain and providing a nucleic acid encoding the humanized variable domains,
i) introducing the monoclonal antibody variable light and heavy chain variable domain encoding nucleic acid in one or more expression vectors for the expression of an (human or humanized) antibody,
j) introducing the expression vector(s) in a cell,
k) cultivating the cell and recovering the antibody from the cell or the cell culture supernatant and thereby producing the antibody.

In one embodiment the obtaining one or more nucleic acids encoding the secreted antibody's variable domains from the B-cell clone comprises the following steps extracting total RNA from the antibody-producing B-cell clone,
performing a single stranded cDNA synthesis/reverse transcription of the extracted polyA$^+$ mRNA,
performing a PCR with a set of species specific primer,
optionally removal of the PCR primer/purification of the PCR product,
optionally sequencing of the PCR product.

In one embodiment the introducing the monoclonal antibody variable light and/or heavy chain variable domain encoding nucleic acid in an expression vector for the expression of an (human or humanized) antibody comprises the following steps T4 polymerase incubation of the variable light and heavy chain variable domain,
linearization and amplification of the expression vector,
T4 polymerase incubation of the amplified expression vector,
sequence and ligation independent cloning of the variable domain encoding nucleic acid into the amplified expression vector, and
preparation of the vector(s) from pool of vector transformed *E. coli* cells.

In one embodiment the methods above comprise immediately prior to the labeling step the following step incubating the population of B-cells with (target) antigen, which is immobilized on a solid surface, and recovering (only) B-cells bound to the immobilized antigen.

In one embodiment the population of B-cells is a non-human animal B-cell population. In one embodiment the B-cell population is a mouse B-cell population, or a hamster B-cell population, or a rabbit B-cell population. In one preferred embodiment the B-cell population is a rabbit B-cell population.

In one embodiment the population of B-cells is obtained from the blood of a non-human animal 4 days after the immunization. In one embodiment the population of B-cells is obtained from the blood of a non-human animal of from 4 days up to at most 9 days after immunization.

In one embodiment the B-cell population is a human B-cell population.

In one embodiment the population of B-cells is obtained from blood by density gradient centrifugation.

In one embodiment the B-cells are mature B-cells.

In one embodiment of the single cells are deposited (individually) into the wells of a multi-well plate.

In one embodiment the antibody is a monoclonal antibody.

In one embodiment the deposited cells are labeled with one or three fluorescence dyes and the incubation is with two to four fluorescently labeled antibodies.

In one embodiment the labeling of the B-cells of the population of B-cells results in labeling of 0.1% to 2.5% of the cells of the (total) B-cell population.

In one embodiment the labeling is of B-cell surface IgG.

In one embodiment the incubation is with a fluorescently labeled anti-IgG antibody and a fluorescently labeled anti-IgM antibody (the labeling is of cell surface IgG and cell surface IgM) and the selection is of cells positive for cell surface IgG and negative for cell surface IgM (results in single cell deposition of $IgG^+IgM^-$-B-cells).

In one embodiment of all aspects the incubation is with a fluorescently labeled anti-IgG antibody and a fluorescently labeled anti-light chain antibody (the labeling is of cell surface IgG and cell surface antibody light chain) and the selection is of cells positive for cell surface IgG and positive for cell surface antibody light chain (results in single cell deposition of $IgG^+LC^+$-B-cells).

In one embodiment the incubation is with a fluorescently labeled anti-IgG antibody and a fluorescently labeled anti-IgM antibody (the labeling is of cell surface IgG and cell surface IgM) and the selection is of cells positive for cell surface IgG and negative for cell surface IgM (results in single cell deposition of $IgG^+IgM^-$-B-cells), whereby the population of B-cells has been incubated with (target) antigen, which is immobilized on a solid surface, and (only) B-cells bound to the immobilized antigen have been recovered and subjected to the incubation with the fluorescently labeled antibodies.

In one embodiment the incubation is with a fluorescently labeled anti-IgG antibody and a fluorescently labeled anti-CD19 antibody (the labeling is of cell surface IgG and cell surface CD19) and the selection is of cells positive for cell surface IgG and also positive for cell surface CD19 (results in single cell deposition of $IgG\pm CD19^+$-B-cells).

In one embodiment the incubation is in addition with a fluorescently labeled anti-light chain antibody (the labeling is of cell surface antibody light chain in addition to the other two labels) and the selection is of cells positive for cell surface antibody light chain (results in single cell deposition of $LC^+$-B-cells).

In one embodiment the B-cell population is a rabbit B-cell population and the incubation is with a fluorescently labeled anti-IgG antibody (the labeling is of cell surface IgG) and the selection is of cells positive for cell surface IgG (results in single cell deposition of $IgG^+$-B-cells).

In one preferred embodiment the B-cell population is a rabbit B-cell population and the incubation is with a fluorescently labeled anti-IgG antibody and a fluorescently labeled anti-IgM antibody (the labeling is of cell surface IgG and cell surface IgM) and the selection is of cells positive for cell surface IgG and negative for cell surface IgM (results in single cell deposition of $IgG^+IgM^-$-B-cells).

In one embodiment the incubation of the rabbit B-cells is in addition with a fluorescently labeled anti-light chain antibody (the labeling is of cell surface antibody light chain in addition to the other two labels) and the selection is of cells positive for cell surface antibody light chain (results in single cell deposition of $LC^+$-B-cells).

In one embodiment the co-cultivating is in a co-cultivation medium comprising RPMI (1640) medium supplemented with 10% (v/v) FCS, 1% (w/v) of a 200 mM glutamine solution that comprises penicillin and streptomycin, 2% (v/v) of a 100 mM sodium pyruvate solution, and 1% (v/v) of a 1 M 2-(4-(2-hydroxyethyl)-1-piperazine)-ethane sulfonic acid (HEPES) buffer. In one embodiment the co-cultivation medium further comprises 0.05 mM beta-mercaptoethanol.

In one embodiment the animal is an experimental animal. In one embodiment the experimental animal is selected from mouse, hamster, and rabbit. In one embodiment the experimental animal is a rabbit.

The following FIGURE and examples are provided to aid the understanding of the present invention, the true scope of which is set forth in the appended claims. It is understood that modifications can be made in the procedures set forth without departing from the spirit of the invention.

DESCRIPTION OF THE FIGURE

FIG. 1 shows the lot-to-lot variability of TSN lots produced with a method known from the art (left part) and with the inventive method as reported herein (right part). Solid square: ratio of the number IgG-positive wells of the respective TSN lot to the number of IgG-positive wells obtained with a reference TSN lot; dash-point-dash line: average of the ratio of the number of IgG positive wells; solid triangles: ratio of the average IgG concentration in the wells obtained with the respective TSN lot to the average IgG concentration in the wells obtained with a reference TSN lot; dashed line: average of the IgG concentration ratios.

EXAMPLES

Materials and Methods

Recombinant DNA techniques

Standard methods were used to manipulate DNA as described in Sambrook, J., et al., Molecular Cloning: A Laboratory Manual, Cold Spring Harbor Laboratory Press, Cold Spring Harbor, New York (1989). The molecular biological reagents were used according to the manufacturer's instructions.

Media and Buffers

Blocking buffer for ELISA comprises 1×PBS and 1% BSA.

Coating buffer for ELISA comprises 4.29 g Na2CO3*10 $H_2O$ and 2.93 g NaHCO3 add water to a final volume of 1 liter, pH 9.6 adjusted with 2 N HCl.

Ethanol-solution for RNA isolation comprises 70% Ethanol or 80% Ethanol.

FACS-buffer for immuno fluorescence staining comprises 1×PBS and 0.1% BSA.

IMDM-buffer for ELISA comprises 1×PBS, 5% IMDM and 0.5% BSA.

Incubation buffer 1 for ELISA comprises 1×PBS, 0.5% CroteinC.

Incubation buffer 2 for ELISA comprises 1×PBS, 0.5% CroteinC and 0.02% Tween 20.

Incubation buffer 3 for ELISA comprises 1×PBS, 0.1% BSA.

Incubation buffer 4 for ELISA comprises 1×PBS, 0.5% BSA, 0.05% Tween, PBS (10×), 0.01 M KH2PO4, 0.1 M Na2HPO4, 1.37 M NaCl, 0.027 M KCl, pH 7.0.

PCR-buffer comprises 500 mM KCl, 15 mM MgCl2, 100 mM Tris/HCl, pH 9.0.

Wash buffer 1 for ELISA comprises 1×PBS, 0.05% Tween 20.

Wash buffer 2 for ELISA comprises 1×PBS, 0.1% Tween 20. Wash buffer 3 for ELISA comprises water, 0.9% NaCl, 0.05% Tween 20.

EL-4 B5 medium comprises RPMI 1640 (Pan Biotech, Aidenbach, Germany) supplemented with 10% FCS (Hyclone, Logan, UT, USA), 2 mM Glutamine, 1% penicillin/streptomycin solution (PAA, Pasching, Austria), 2 mM sodium pyruvate, 10 mM HEPES (PAN Biotech, Aidenbach, Germany) and 0.05 mM β-mercaptoethanol (Gibco, Paisley, Scotland).

Animal Care

The experimental animals were held according to the German animal protection law (TierSCHG) as well as according to the respective European guidelines.

Mice and hamster were received at an age of from 6 to 8 weeks and were immunized prior to an age of 12 weeks. The antigen was at first applied together with complete Freud's adjuvant (CFA). Further applications were with incomplete Freud's adjuvant (IFA). The antigen containing emulsion was applied subcutaneously whereby the emulsion comprised an amount of from 50 to 100 μg antigen depending on the weight of the receiving experimental animal.

Proliferation Assays a) Cell Titer Glo (CTG) Viability Assay

The CTG viability assay (Promega; #G7571) was used according to the instructions of the manufacturer.

b) $^3$H Thymidine Assay

After 6 days of incubation $^3$H-Thymidin was added (0.5 μCi/well) and incubated for further 16 hours. The incorporation of $^3$H-Thymidine during cell proliferation was determined with a microplate scintillation counter (Wallac).

c) Microscopic Analysis

For the acquisition of microscopic images, a phase contrast microscope from Leica (Leica DM IL) combined with a high resolution camera (Leica DFC290 HD) was used.

d) Analysis of B-cell Activation via CFSE-Labeling.

Isolated B-cells were washed with sterile phosphate buffer saline solution (PBS). Up to $1\times10^7$ cells were resuspended in 1 ml protein-free PBS and incubated with CFSE (#C34554, Invitrogen/Molecular Probes) for 3 to 10 minutes at a final concentration of 2.5 μM at 37° C. CFSE loading was stopped by addition of an excess of FCS-supplemented medium. After extensive washing with FCS-containing medium, B-cells were used in co-culture experiments. Proliferation of CD19$^+$ gated (B−)cells as a consequence of CFSE dilution was confirmed by flow cytometric analysis (FL-1 channel) after indicated time points.

Quantification of IgG

The 96-well multi well plate in which the co-cultivation was performed was centrifuged after seven days of co-cultivation at 300×g for 5 min. 150 μl supernatant was removed and diluted at a ratio of 2:1 with PBS in a second 96-well multi well plate.

The antibody was used at a concentration of 50 ng/ml. If the OD was or exceeded 1 after an incubation time of 5 min. a dilution series of from 0.8 to 108 ng/ml IgG was tested.

Panning on Antigen a) Coating of Plates

Biotin/Streptavidin: Sterile streptavidin-coated 6-well plates (cell culture grade) were incubated with biotinylated antigen at a concentration of 0.5-1(2) μg/ml in PBS at room temperature for one hour. Plates were washed in sterile PBS three times before use.

Covalently bound protein: Sterile cell culture 6-well plates were coated with 2 μg/ml protein in carbonate buffer (0.1 M sodium bicarbonate, 34 mM disodium hydrogen carbonate, pH 9.55) over night at 4° C. Plates were washed in sterile PBS three times before use.

b) Panning of B-Cells on Peptides 6-well tissue culture plates coated with the respective antigen were seeded with up to $6\times10^6$ cells per 4 ml medium and allowed to bind for one hour at 37° C. in the incubator. Non-adherent cells were removed by carefully washing the wells 1-2 times with 1×PBS. The remaining sticky cells were detached by trypsin for 10 min. at 37° C. in the incubator and then washed twice in media. The cells were kept on ice until the immune fluorescence staining.

Gene Synthesis

Desired gene segments encoding cDNA were prepared by Geneart GmbH (Regensburg, Germany). The gene segments are flanked by singular restriction endonuclease cleavage sites to facilitate expression construct cloning as described below. The DNA sequence of the subcloned gene fragments were confirmed by DNA sequencing.

Rabbit B-Cell Medium/EL4-B5 Medium:

| | | | | |
|---|---|---|---|---|
| 500 | ml | RPMI 1640 | #P04-17500 | PAN Biotech |
| 50 | ml | FCS | #A15-512 | PAA |
| 5 | ml | L-glutamine | #25030-024 | Invitrogen |
| 5 | ml | potassium pyruvate | #P04-43100 | PAN Biotech |
| 5 | ml | HEPES | #15630-056 | Invitrogen |
| 500 | μl | β-mercaptoethanol | #31350010 | Invitrogen |
| 1 | ml | Pen/Strep | #11074440001 | Roche Dia. GmbH |

Additives to Rabbit B-Cell Medium

| | | |
|---|---|---|
| SAC | #507858 | Calbiochem |

Multi-Well-Plates

| | | |
|---|---|---|
| 96erU-plate | #3799 | Corning |

Phenotyping/Sorting of Antibodies

| | | |
|---|---|---|
| goat anti-rabbit IgG Fc-antibody anti-human/murine (rabbit cross-reactive) | AbDSerotec | STAR121F |
| anti CD40L antibody: | | |
| anti-muCD40L antibody | R&D systems | AF1163 |
| anti-huCD40L antibody | &D systems | AF617R |
| donkey anti-goat IgG antibody Alexa 488 | Molecular Probes | A11055 |

Miscellaneous

| | | |
|---|---|---|
| anti-FITC antibody-coupled microbeads | Miltenyi Biotec | #130-048-701 |
| human B-cell negative isolation kit | Invitrogen | #113.13D |
| Nucleofector Kit T | Lonza | VCA-1002 |
| CBA for total IgG | BD Biosciences | #558679 |

Example 1

Immunization of Rabbits

NZW rabbits (Charles River Laboratories International, Inc.) were used for immunization. The antigen was solved in $K_3PO_4$ buffer pH 7.0 at a concentration of 1 mg/ml and mixed (1:1) with complete Freud's adjuvant (CFA) till generation of stabile emulsion. The rabbits received an intra-dermal (i.d.) injection of 2 ml of emulsion followed by a second intra muscular (i.m.) and third subcutaneous (s.c.) injection each with 1 ml in one week interval. The fourth i.m. injection of 1 ml was performed two weeks later followed by two further s.c. injections of 1 ml in four weeks interval.

During the immunization serum antibody titer was determined with an antigen specific assay. At an antibody titer with an $IC_{50}$ of 1:10000 the blood or the spleen of the immunized animal was removed. For reactivation of antigen specific B-cells 30 μg to 50 μg of the antigen was applied intravenously to the experimental animal three days prior to the removal of the blood or the spleen.

Example 2

Removal of Organs, Blood and Macrophages

Blood from rabbits was obtained by punctuation of the ear vein or, for larger volumes, of the ear artery. Whole blood (10 ml) was collected from rabbits 4-6 days after the third, fourth, fifth and sixth immunization and used for single cell sorting by FACS.

Macrophages were isolated from the obtained blood by attachment to cell culture plastic.

If a larger amount of was required, peritoneal macrophages were isolated. For this the animals have to be at least 3 months of age. For the removal of peritoneal macrophages, animals were sacrificed and 5 ml of EL-4 B5 medium with a temperature of 37° C. was immediately injected into the peritoneal cavity. After kneading the animal's belly for 5 minutes, the solution containing the cells was removed.

EDTA containing whole blood was diluted twofold with 1×PBS before density centrifugation on lympholyte mammal (Cedarlane Laboratories) or Ficoll Paque Plus (GE Healthcare, cat. #17-1440-03), which was performed to isolate rabbit PBMC. PBMCs were washed twice before staining with antibodies.

Example 3

Density Gradient Centrifugation

The isolation of peripheral blood mononuclear cells (PBMCs) was effected by density gradient separation with Lympholyte® according to manufacturer's instructions A (Lympholyte®-mammal, Cedarlane).

Withdrawn blood (optionally supplemented with EDTA) was diluted 1:1 with phosphate buffered saline (PBS), e.g. 60 ml blood plus 60 ml buffer. In a centrifuge vial the same volume of density separation medium was provided and the diluted blood is carefully added via the wall of the vial on top of the density separation medium. The ratio of the density separation medium to the PBS-diluted blood is about 1:1.5. Depending on the total volume of diluted blood a certain number of vials will be required. The vials were centrifuged for 20 min. at 800×g without braking. Each individual white interim layer was added to 25 ml PBS, supplemented with PBS to a total of 50 ml and centrifuged at 800×g for 10 min. The supernatants were discarded, the pellet were resuspended in 1/120 of the final volume of PBS, pellets were combined on a 1:1 basis and PBS was added to a final volume of 50 ml. Thereafter the vials were centrifuged again. Depending on the number of blood samples the samples are combined on a 1:1 ratio after each centrifugation step until only one sample is left. The final pellet was resuspended in PBS.

Example 4

Hypotonic Lysis of Red Blood Cells

For disruption of red blood cells by hypotonic lysis an ammonium chloride solution (BD Lyse™) was diluted 1:10 with water and added at a ratio of 1:16 to whole blood. For lysis of the red blood cells the mixture was incubated for 15 min. in the dark. For separation of cell debris from intact cells the solution was centrifuged for 10 min. at 800×g. The supernatant was discarded, the pellet was resuspended in PBS, washed again, centrifuged and the pellet was resuspended in PBS. Example 8

Example 5

Depletion of Macrophages

Sterile 6-well plates (cell culture grade) were used to deplete macrophages and monocytes through unspecific adhesion. Wells were either coated with KLH (keyhole limpet haemocyanine) or with streptavidin and the control peptides. Each well was filled with 3 ml to (at maximum) 4 ml medium and up to $6 \times 10^6$ peripheral blood mononuclear cells from the immunized rabbit and allowed to bind for 60 to 90 min. at 37° C. in the incubator. Thereafter the lymphocyte containing supernatant was transferred to a centrifugation vial and centrifuged at 800×g for 10 min. The pellet was resuspended in PBS.

Example 6

Enrichment of Antigen-Specific B-Cells

The respective antigen was diluted with coating buffer to a final concentration of 2 μg/ml. 3 ml of this solution were added to the well of a 6-well multi well plate and incubated over night at room temperature. Prior to use the supernatant was removed and the wells were washed twice with PBS. The B-cell solution was adjusted to a cell density of $2 \times 10^6$ cells/ml and 3 ml are added to each well (up to $6 \times 10^6$ cells per 3-4 ml medium) of a 6-well multi well plate. The plate was incubated for 60 to 90 min. at 37° C. The supernatant was removed and non-adherent cells were removed by carefully washing the wells 1-4 times with 1×PBS. For recovery of the sticky antigen-specific B-cells 1 ml of a trypsin/EDTA-solution was added to the wells of the multi well plate and incubated for 10 to 15 min. at 37° C. The incubation was stopped by addition of medium and the supernatant was transferred to a centrifugation vial. The wells were washed twice with PBS and the supernatants were combined with the other supernatants. The cells were pelleted by centrifugation for 10 min. at 800×g. The cells were kept on ice until the immune fluorescence staining. The pellet was optionally resuspended in PBS.

Example 7

Cultivation of T-Cells

The T-cells were isolated from the thymus of 3-4 week old mice and hamsters, or of 4-5 week old rabbits, respectively. The cells were centrifuged and immediately cultivated or frozen in aliquots of 4-5×$10^7$ cells. The thymocytes were seeded with a minimum cell density of 5×$10^5$ cells/ml of EL-4 B5 medium in 175 $cm^2$ culture flasks and incubated for up to 48 hours (40-48 hours depending on the TSN production method the macrophages will be used in; see Examples 9 and 10) at 37° C.

Example 8

Cultivation of Macrophages

Macrophages were isolated from the peritoneal cavity of mice and hamsters, respectively, of an age of at least three months. Peritoneal macrophages from mice or hamsters, or blood mononuclear cells from rabbits were cultivated in EL-4 B5 medium at a cell density of at least 1×$10^5$ cells/ml in 175 $cm^2$ culture flasks for 1.5 hours at 37° C. Afterwards the medium was removed and non-attached cells were removed from the attached macrophages by washing with warm EL-4 B5 medium, followed by cultivation for about 48 hours in 35 ml medium.

Example 9

Co-Cultivation of T-Cells and Macrophages According to the Current Invention

T-cells (see Example 7, 40 hours cultivation) and macrophages (see Example 8) were cultivated in separate flasks. Prior to combining both cell populations, the T-cells were centrifuged for 10 min. at 800×g. The supernatant was discarded and the cell pellet was resuspended in 10 ml EL-4 B5 medium. The final cultivation medium contained T-cells adjusted to a cell density of 5×$10^5$ cells/ml, 10 ng phorbol-12-myristate-13-acetate (PMA) per ml of medium, and 5 µg phytohemagglutinin M (PHA-M) per ml of medium (=T-cell suspension). Thereafter, the cultivation medium was removed from the macrophages (=medium-depleted macrophages). An amount/volume of the T-cell suspension was added to the flasks containing the medium-depleted macrophages to obtain a final but defined macrophage cell density of from 1.25-2×$10^6$ macrophages/ml. After 30-46 hours of co-cultivation, the cultivation medium was removed and was termed TSN solution. For removal of remaining cells the TSN solution was filtered through a 0.22 µm filter. The TSN solution was frozen at −80° C. in aliquots (of 4.2 ml).

Example 10—Comparative Example

Co-Cultivation of T-Cells and Macrophages According to the State of the Art

T-cells (see Example 7, 48 hours cultivation) and macrophages (see Example 8) were cultivated in separate flasks. Prior to combining both cell populations, the T-cells were centrifuged for 10 min. at 800×g. The supernatant was discarded and the cell pellet was resuspended in 10 ml EL-4 B5 medium. The final cultivation medium contained T-cells adjusted to a cell density of 5×$10^5$ cells/ml, 10 ng phorbol-12-myristate-13-acetate (PMA) per ml of medium, and 5 µg phytohemagglutinin M (PHA-M) per ml of medium (=T-cell suspension). Thereafter, the cultivation medium was removed from the macrophages (=medium-depleted macrophages). An amount/volume of the T-cell suspension was added to the flasks containing the medium-depleted macrophages to obtain a final macrophage cell density of 1×$10^6$ macrophages/ml. After 36 hours of co-cultivation, the cultivation medium was removed and was termed TSN solution. For removal of remaining cells the TSN solution was filtered through a 0.22 µm filter. The TSN solution was frozen at −80° C. in aliquots (of 4 ml).

Example 11

Cultivation of EL-4 B5 Cells

The frozen EL-4 B5 cells were thawed rapidly in a water bath at 37° C. and diluted with 10 ml EL-4 B5 medium. After centrifugation at 300×g for 10 minutes the supernatant was discarded and the pellet resuspended in 1 ml medium.

The EL-4 B5 cells were inoculated at a cell density of 8×10 cells/ml in T175 cultivation flasks. Cell density was determined every second day and adjusted to 8×$10^4$ cells/ml. The cells have a doubling time of approximately 10 hours.

Cells were harvested and adjusted to a cell density of 1×$10^6$ cells/ml before y-irradiation at 50 Gy.

Example 12

Co-Cultivation of B-Cells and EL-4 B5 Cells

Single sorted B-cells were cultured in 96-well plates with 210 µl/well EL-4 B5 medium with Pansorbin Cells (1:20000) (Calbiochem (Merck), Darmstadt, Deutschland), 5% thymocyte supernatant produced according to Example 9 or 10 and gamma-irradiated EL-4-B5 murine thymoma cells (2×$10^4$/well) for 7 days at 37° C. in an atmosphere of 5% $CO_2$ in the incubator. B-cell culture supernatants were removed for screening and the cells harvested immediately for variable region gene cloning or frozen at −80° C. in 100 ill RLT buffer (Qiagen, Hilden, Germany).

It has been found that depending on the amount of macrophages present in the co-cultivation of thymocytes (T-cells) with mononuclear cells (macrophages), i.e. depending on the ratio of said cells, the produced TSN shows different properties. The respective results are shown in the following Table 5 (total wells=4*84). The reference value was obtained with the comparative state of the art method according to Example 10.

TABLE 5

| ratio [*$10^6$ cells/ml] thymocytes:mononuclear cells | average IgG positive wells [n] | average frequency of IgG positive wells [% of total wells] | average productivity of all IgG positive wells [µg/ml] | example |
|---|---|---|---|---|
| 0.5:1 (ref.) | 33.3 ± 2.3 | 39.6 ± 2.7 | 0.35 ± 0.05 | 10 |
| 0.5:1.25 | 38.8 ± 4.8 | 46.1 ± 5.7 | 0.81 ± 0.10 | 9 |
| 0.5:1.5 | 34.5 ± 5.5 | 41.1 ± 6.6 | 1.22 ± 0.12 | 9 |
| 0.5:2 | 37.3 ± 1.8 | 44.4 ± 2.1 | 1.32 ± 0.23 | 9 |

Example 13

Co-Cultivation of B-Cells and EL-4 B5 Cells with Different Lots Produced According to Examples 9 and 10

To show the robustness of the herein reported TSN production method compared to the method known from the art multiple lots have been prepared with the methods according to Examples 9 and 10. The results are presented in the following Tables 6 and 7.

TABLE 6

| According to Example 10: | | |
|---|---|---|
| TSN lot | ratio IgG positive wells to reference | ratio average productivity wells to reference |
| reference | 1.00 | 1.00 |
| 1 | 0.80 | 0.75 |
| 2 | 0.83 | 0.89 |
| 3 | 0.84 | 0.65 |
| 4 | 0.78 | 0.42 |
| 5 | 1.04 | 0.49 |
| 6 | 0.88 | 0.56 |
| 7 | 0.96 | 0.64 |
| 8 | 0.94 | 0.69 |
| 9 | 1.11 | 0.79 |
| 10 | 0.83 | 0.66 |
| 11 | 1.11 | 0.39 |
| 12 | 1.04 | 0.78 |
| 13 | 0.95 | 0.48 |
| average | 0.93 | 0.63 |

TABLE 7

| According to example 9: | | |
|---|---|---|
| TSN lot | ratio IgG positive wells to reference | ratio average productivity wells to reference |
| reference | 1.00 | 1.00 |
| 14 | 0.83 | 0.52 |
| 15 | 0.96 | 0.96 |
| 16 | 0.99 | 1.55 |
| 17 | 1.04 | 1.15 |
| 18 | 0.98 | 1.21 |
| 19 | 1.33 | 1.53 |
| 20 | 0.81 | 1.37 |
| 21 | 1.05 | 1.54 |
| 22 | 1.01 | 1.09 |
| 23 | 1.14 | 1.26 |
| 24 | 1.23 | 1.02 |
| 25 | 1.03 | 1.38 |
| 26 | 1.03 | 0.96 |
| 27 | 1.04 | 1.31 |
| 28 | 1.17 | 1.52 |
| 29 | 1.10 | 1.46 |
| 30 | 1.00 | 1.95 |
| 31 | 0.97 | 2.60 |
| 32 | 0.94 | 1.27 |
| 33 | 0.94 | 1.15 |
| 34 | 0.85 | 1.05 |

TABLE 7-continued

| According to example 9: | | |
|---|---|---|
| TSN lot | ratio IgG positive wells to reference | ratio average productivity wells to reference |
| 35 | 0.96 | 1.32 |
| average | 1.02 | 1.33 |

The invention claimed is:

1. A method for co-cultivating one or more B-cells, comprising:

co-cultivating the one or more B-cells with EL4-B5 cells in the presence of thymocyte supernatant (TSN);

wherein the TSN is produced according to a method comprising the steps, (a) co-cultivating thymocytes and macrophages at a cell ratio of 0.5:1.2 to 0.5:2 in the presence of phorbol-12-myristate-13-acetate and phytohemagglutinin M for up to 60 hours, and (b) separating the co-cultivation medium from the cells and thereby producing the thymocyte supernatant.

2. The method according to claim 1, wherein the thymocytes and macrophages cell ratio is 0.5:2.

3. The method according to claim 1, wherein the thymocyte cell density is $5\times10^5$ cells/ml in step (a).

4. The method according to claim 1, wherein prior to step (a), the thymocytes are incubated for up to 60 hours at 37° C. in cultivation medium.

5. The method according to claim 1, wherein the macrophages are isolated from Peripheral Blood Mononuclear Cells (PBMC) by adherence to a solid surface at a cell density of $2\times10^6$ cells/ml and the attached macrophages are incubated for 40 hours in cultivation medium prior to step (a).

6. The method according to claim 1, wherein prior to step (a) cultivation medium of the thymocytes is replaced by fresh medium containing 10 ng/ml phorbol-12-myristate-13-acetate (PMA) and 5 pg/ml phytohemagglutinin M (PHA-M).

7. The method according to claim 1, wherein step (a) is started by removing cultivation medium from the macrophages and adding the thymocyte suspension.

8. The method according to claim 1, wherein the one or more B-cells are co-cultivated in a medium, and the medium is RPMI medium supplemented with 10% (v/v) Fetal Calf Serum (FCS), 1% (w/v) of a 200 mM glutamine solution that comprises penicillin and streptomycin, 2% (v/v) of a 100 mM sodium pyruvate solution, and 1% (v/v) of a 1 M 2-(4-(2-hydroxyethyl)-1-piperazine)-ethane sulfonic acid (HEPES) buffer, further comprising 0.05 pM 0-mercapto-ethanol.

* * * * *